United States Patent
Peters et al.

[11] Patent Number: 5,830,195
[45] Date of Patent: Nov. 3, 1998

[54] COUPLINGS FOR MEDICAL CANNULAE

[75] Inventors: Joseph L. Peters, Ware; James W. Kerr, New Cotessey, both of England

[73] Assignee: Clinical Product Development Limited, London, England

[21] Appl. No.: 687,384

[22] PCT Filed: Feb. 17, 1995

[86] PCT No.: PCT/GB95/00337

§ 371 Date: Aug. 19, 1996

§ 102(e) Date: Aug. 19, 1996

[87] PCT Pub. No.: WO95/22369

PCT Pub. Date: Aug. 24, 1995

[30] Foreign Application Priority Data

Feb. 17, 1994 [GB] United Kingdom ............ 9403021

[51] Int. Cl.⁶ ............................................. A61M 25/00
[52] U.S. Cl. ............................................. 604/283; 604/905
[58] Field of Search .................................. 604/283, 280, 604/240–243, 905

[56] References Cited

U.S. PATENT DOCUMENTS 5,000,739   3/1991   Kulisz et al. .

FOREIGN PATENT DOCUMENTS

| | | |
|---|---|---|
| 0031022 | 7/1981 | European Pat. Off. . |
| 0098103 | 1/1984 | European Pat. Off. . |
| 0217055 | 4/1987 | European Pat. Off. . |
| 0227219 | 7/1987 | European Pat. Off. . |
| 0248979 | 12/1987 | European Pat. Off. . |
| 0415665 | 3/1991 | European Pat. Off. . |
| 0443868 | 8/1991 | European Pat. Off. . |
| 0471574 | 2/1992 | European Pat. Off. . |
| 4318101 | 12/1994 | Germany . |
| 670955 | 7/1989 | Switzerland . |
| 2146405 | 4/1985 | United Kingdom . |
| 2202747 | 10/1988 | United Kingdom . |

*Primary Examiner*—John D. Yasko
*Attorney, Agent, or Firm*—Watson Cole Grindle Watson, P.L.L.C.

[57] ABSTRACT

A medical coupling has male and female members (1, 2) which push fit together, and a screw cap (7) which secures the members against separation. To prevent unintentional release of the cap, locking means, such as a ratchet and pawl mechanism, are provided between the cap and female member. An outer shell (25) can enclose the cap for providing an enclosure around the fluid connection to deter bacterial contamination. Alternatively a separate capsule can enclose the coupling for this purpose. The two members and cap are connectable by holding gripping portions which are located remotely from the parts forming the fluid connection to reduce risk of contamination. A valve system is associated with the female member for closing a flexible tube connected to this member and to displace liquid to fill the space left in this member when the male member is disconnected from it.

22 Claims, 12 Drawing Sheets

COUPLINGS FOR MEDICAL CANNULAE

This invention is concerned with medical equipment, and in particular relates to couplings for connecting cannulae or catheters to a connection tube through which liquid to be administered to a patient is delivered, or fluid to be taken from a patient is collected.

It is generally accepted practice for a catheter tube to be equipped, at the end thereof opposite the end which is introduced into the patient, with a moulded plastic connection hub defining a tapered socket of frustoconical configuration. This hub constitutes a female coupling member for cooperation with a complementary male member fitted to the end of the connection tube, e.g. of an administration set. The male member comprises a tapered frustoconical spigot which is dimensioned to engage with a friction fit in the tapered socket of the catheter hub. Thus, the coupling is made by pushing the male and female members together, and is disconnected simply by pulling the members apart. If a coupling should become separated unintentionally, there may be very serious consequences for the patient e.g. as a result of air being drawn in through the catheter and entering the blood stream. Various proposals have been put forward for applying safety devices to hold the members of the coupling against accidental separation, but none have gained practical acceptance, except that a small rotatable cap is sometimes provided, either held captive with the male member or loosely received on the connection tube attached to it, and this can has an internal thread which allows it to be screwed over the catheter hub by cooperation with a pair of small radial lips formed at its free end. However, this cap can become unscrewed and it is not always completely reliable, e.g. in a situation where a patient has a tendency to fiddle with equipment. Therefore, it is common practice for medical staff to wrap tape around the coupling. While tape helps to secure the coupling, it is inconvenient and has the disadvantage that the coupling is concealed from sight.

Another disadvantage of the conventional coupling is that the male and female members are quite small and need to be held in the fingers at or very closely to those surface portions which are contacted by fluid, when engaging and releasing the coupling. This carries with it a risk of infection as bacteria deposited on the plastic members have a tendency to colonise and the bacteria can be carried by the liquid flowing through the coupling into the patient's blood stream. Also, the patient may finger the coupling and cause bacterial contamination.

When the known coupling is released, for example for replacement of the administration set, there is a danger that air may enter the catheter through the open socket of the connection hub. While a device to pinch closed the catheter tube has been proposed, this does not provide a complete solution. When the male coupling member is withdrawn from the socket, there is left a space which naturally fills with air, and upon another male member being inserted into the socket it is possible for a bubble or air to become trapped within the coupling and subsequently pass through the catheter into the patient.

The present invention addresses the foregoing problems.

In accordance with one aspect the present invention resides broadly in a coupling for a medical cannula comprising two members secured against separation by a rotatably tightened part, characterised in that a locking arrangement is provided for locking said part against rotation in the loosening direction.

Stated more specifically the invention provides a coupling for a medical catheter, comprising separate male and female members which are connectable with a push fit, a cap for surrounding the members and rotatable for releasable engagement with one of the members to secure the members against being pulled apart, and means on said cap and said one member for locking the cap against reverse rotation.

In a particular embodiment, the said one member is the catheter hub and includes a peripheral surface portion provided with ratchet teeth therearound. The cap, held captive but rotatable on the male member, has an internally threaded section and projecting forwardly therefrom means carrying one or more pawls for engaging the ratchet teeth to retain the cap against rotation in a direction to release the cap. The means carrying the pawls is preferably resilient to allow for their disengagement from the ratchet teeth when authorised separation of the coupling is required. By these locking means the male and female members are positively held against unintentional disconnection and the chances of them becoming separated inadvertently are extremely remote.

According to a second aspect of the present invention there is provided a coupling for a medical catheter comprising separate male and female members which are connectable with a push fit, a cap for surrounding the members and rotatable for releasable engagement with one of the members to secure the members against being pulled apart, and means extending rearwardly of the cap part engageable with the one member and defining at a position remote therefrom a holding section for holding the cap during connection of the male and female members and rotation of the cap for engaging said cap part with said one member.

The rearwardly extending means may be fastened to, e.g. be integral with the cap, or it may be a separate component, in which case it can be adjustable and define a shell or housing for enclosing the assembled male and female members, and the cap, to form a barrier against bacterial contaminations. In either case, because the coupling can be completed and secured without need to handle any parts in close proximity to the cooperating portions of the male and female members, the risk of these portions being contacted by bacteria is substantially eliminated.

In accordance with a third aspect of the invention there is provided a coupling for a medical catheter comprising a female member for cooperation with a male coupling member, a flexible walled tube connected to the female member, and valve means for pinching closed the tube and displacing liquid therein towards the female member for filling the volume occupied by the male member on disconnection of the male member from the female member.

By virtue of the valve means the liquid remaining in the catheter can be brought to fill the socket of the catheter hub and thereby risk of air passing through the catheter during and immediately after an administration set replacement operation is excluded. The valve means can take a variety of different forms and will be operated by initially closing the tube at one position followed by reducing the volume within the tube on the upstream side of this position.

Provided in accordance with a fourth aspect of the invention there is a coupling for a medical catheter comprising two separate members releasably engageable with each other, and a capsule for defining a substantially sealed enclosure around the engaged coupling members for excluding bacteria from contact therewith.

The capsule conveniently comprises two parts, e.g. connected by an integral hinge, adapted to engage with a snap fit when applied over the coupled members, and can be capable of being opened only by destruction to thwart any attempt to re-use a capsule which may have become contaminated.

A better understanding of the invention and its several aspects will be gained from the detailed description which follows, reference being made to the accompanying drawings in which.

Figure 1:
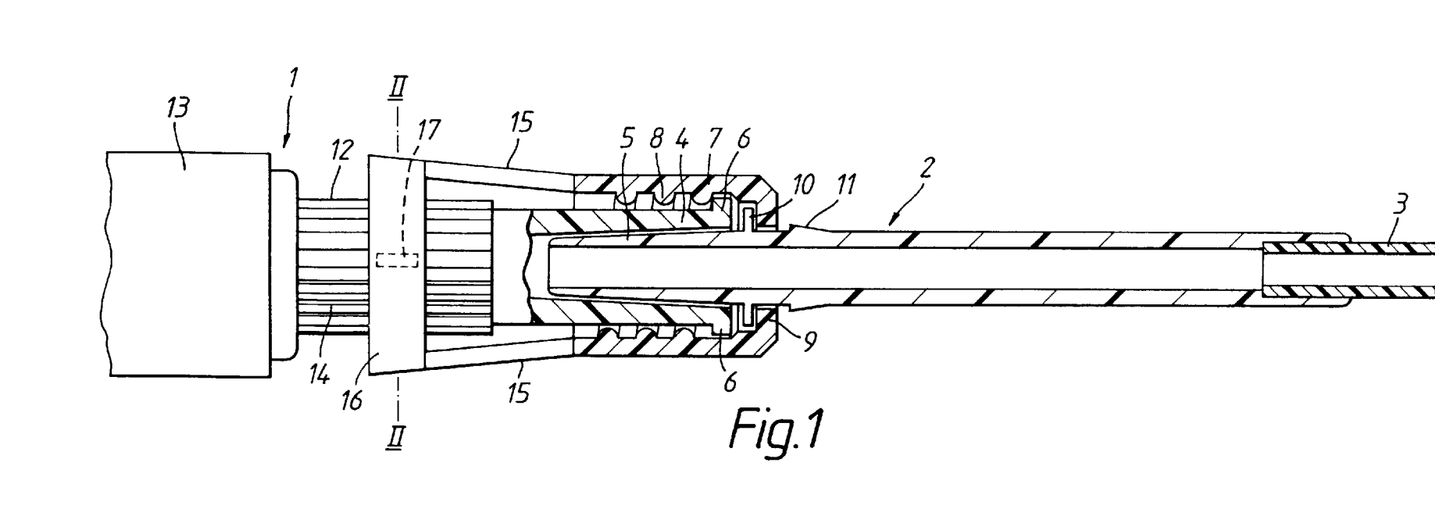
FIG. 1 is a partly sectioned side elevation of a coupling embodying the invention.

The coupling assembly illustrated in FIG. 1 comprises a female member 1 in the form of a rigid plastics moulding fixed to the trailing end of a catheter tube (not shown), and a male member 2 attached to a connection tube 3, e.g. leading from a fluid container. The female member includes a part 4 defining a tapered socket into which a complementary spigot 5 of the male member is engaged and sealed with a friction push-fit. At the socket mouth the part 4 is provided with a pair of opposed radially directed lips 6 for engagement by a cap 7 which has a cylindrical part provided with an internal screw thread 8 to enable the cap to be screwed onto the part 4 by cooperation of the lips 6 with the thread. The cap has an end wall 9 with a central hole through which the male member 2 passes with a clearance allowing rotation of the cap relative to the male member 2. The end wall 9 abuts a flange 10 formed on member 2 and can be held captive by a further projection 11 on the member 2 although this is not essential. As so far described the coupling is of a construction in practical use and generally known as a "Luer Lock".

Figure 2:
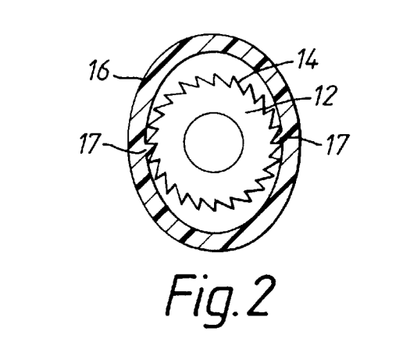
FIG. 2 is a transverse cross section taken along the line II—II in FIG. 1.

In accordance with the present invention the female member includes a locking section 12 located between the part 4 and a holding part 13 for gripping the member when connecting and disconnecting the coupling. The section 12 has longitudinal ratchet teeth 14 around its periphery as clearly shown in FIG. 2. Carried by the cap and attached to the cylindrical part by integral strips 15 or a flexible skirt is an elliptical collar 16 having inwardly directed pawls 17 positioned opposite one another on the smallest diameter of the ellipse. The collar is resilient and the pawls 17 engage the ratchet teeth 14 to allow rotation of the cap about the member 1 in the direction (counterclockwise as seen in FIG. 2) corresponding to forward screwing movement of the cap onto the part 4, and to prevent reverse rotation, i.e. in a direction to disengage the cap from part 4. However, by squeezing the collar In the direction of the greatest diameter of the ellipse, the pawls can be disengaged to permit such reverse rotation and hence release of the cap to allow disconnection of the male and female members. From the foregoing description it will be understood the coupling is made by pushing the spigot 5 into the socket of part 4, advancing the cap 7 to bring the thread 8 into cooperation with the lips 6, and the pawls 17 into cooperation with the ratchet teeth 14, and screwing the cap onto the part 4 of the female member. During this action the pawls, due to their shape, ride over the ratchet teeth, but when the cap is fully screwed on the engagement of the pawls 17 with the ratchet teeth prevents the cap unscrewing inadvertently. To disconnect the coupling the collar 16 is squeezed as described above and turned to unscrew the cap before the members 1, 2 are pulled apart.

Figure 3:
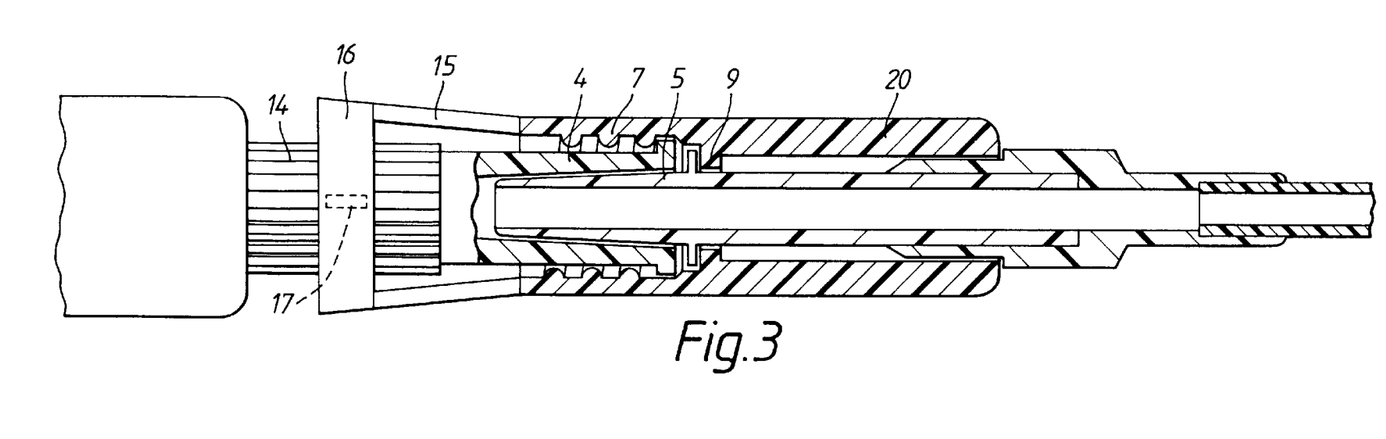
FIG. 3 is a view similar to FIG. 1 showing a modified coupling.
Figure 4:
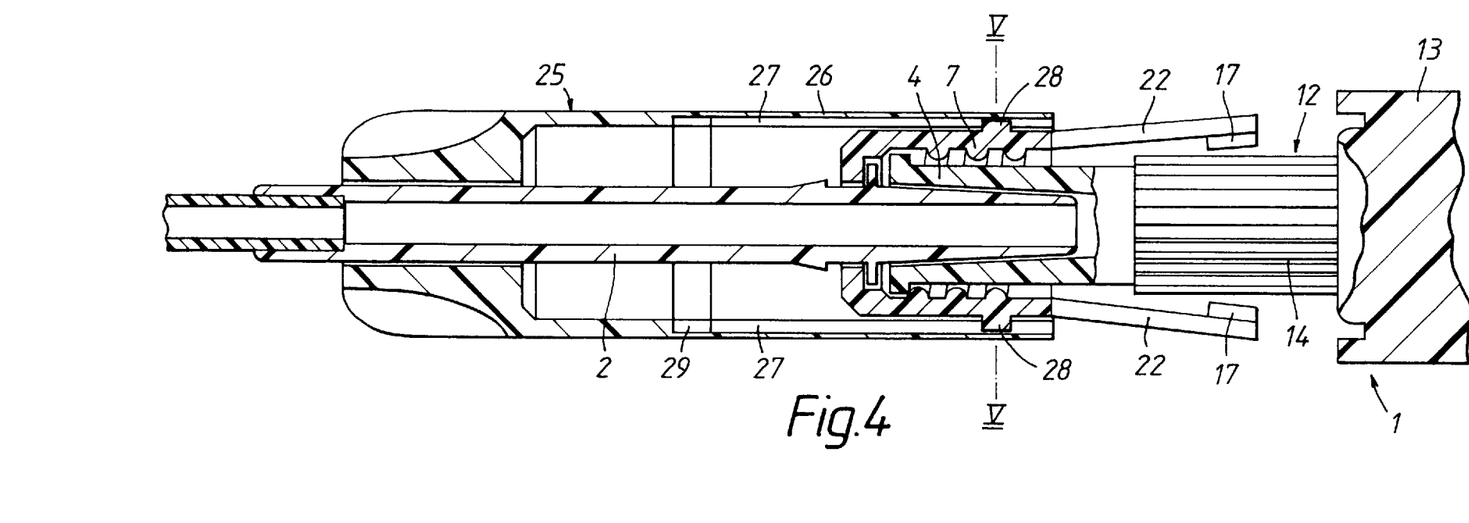
FIG. 4 is a partly sectioned side elevation of another coupling in accordance with the invention.
Figure 5:
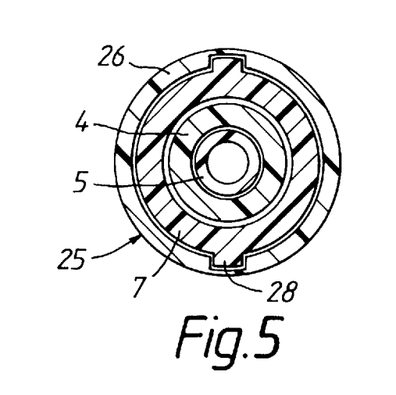
FIG. 5 is a transverse section taken along the line V—V in FIG. 4.
Figure 6:
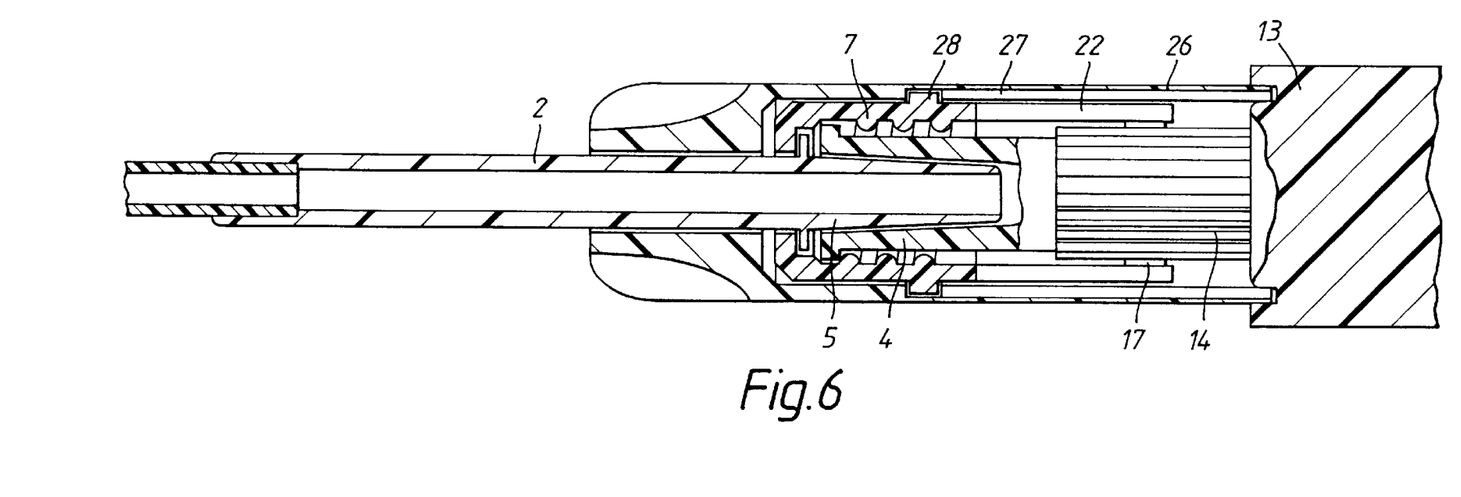
FIG. 6 shows the coupling of FIG. 4 in fully connected condition.

FIG. 3 shows a modified embodiment wherein the can is formed with an extension 20 directed rearwardly from the wall 9. This extension constitutes a finger grip section so that both the can and the female member can be held at locations remote from the spigot 5 and socket part 4, which form the fluid conducting joint between the members, during their connection, and hence risk of contamination by bacteria is reduced. The coupling is otherwise as described above in relation to FIGS. 1 and 2. An alternative coupling assembly also embodying the invention is shown in FIGS. 4 to 6. The male and female members in this embodiment are essentially the same as in the embodiment of FIG. 1, as is the cap 7 except that the pawls 17 are carried at the free ends of resilient arms 22 extending forwardly from the cylindrical cap part. The arms are arranged normally to bias the pawls out of engagement with the ratchet teeth 14 as depicted in FIG. 4. An outer housing member or shell 25 is slidably mounted over the male member 2 and includes a forwardly directed cylindrical skirt 26 which surrounds the cap 7 and spigot 5. On the inside of the skirt are longitudinal grooves 27 defining keyways for key elements in the form of radial projections or studs 28 on the cylindrical part of the cap. Thus, the shell 25 is fast for rotation with the cap 7, but is longitudinally displaceable relative thereto. The trailing end of the shell includes a finger grip portion for holding the male member during connection of the assembly. The spigot 5 is inserted into the socket and the cap 7 is screwed onto the part 4 by rotating the shell and hence the cap relative to the female part 1. During this engagement the pawls 17 are held free of the ratchet teeth. The shell is then displaced forwardly to press the arms 22 inwardly and thereby engage the pawls with the ratchet teeth to lock the shell and cap against rotation in the direction to release the cap, and to bring the leading end of the shell into cooperation with the part 13 of the female member. As shown the part 13 has an annular groove for receiving the end of the shell. In this closed position, as shown in FIG. 6, the shell and part 13 define an enclosure surrounding completely the parts forming the fluid connection to deter bacterial contamination of these parts. By the end of the shell engaging in the groove in the female member there is formed a labyrinth type seal between these parts. If required a detent means could be provided to retain the shell in its closed position. The inner surface of the shell preferably includes an annular groove 29 at the inner end of the keyway grooves 27, the studs 28 being located in this groove when the shell is closed so that the shell can rotate freely in this axial position. It will be understood the shell must be retracted to the position shown in FIG. 4, to release the pawls from the ratchet teeth, before the cap can be unscrewed to release the coupling.

In this embodiment it is not essential for the teeth and pawls to form a ratchet mechanism as they are not engaged until the cap has been screwed home. Thus, the locking section 12 could have longitudinal splines with which the pawls engage to prevent rotation of the cap in either direction.

Figure 7:
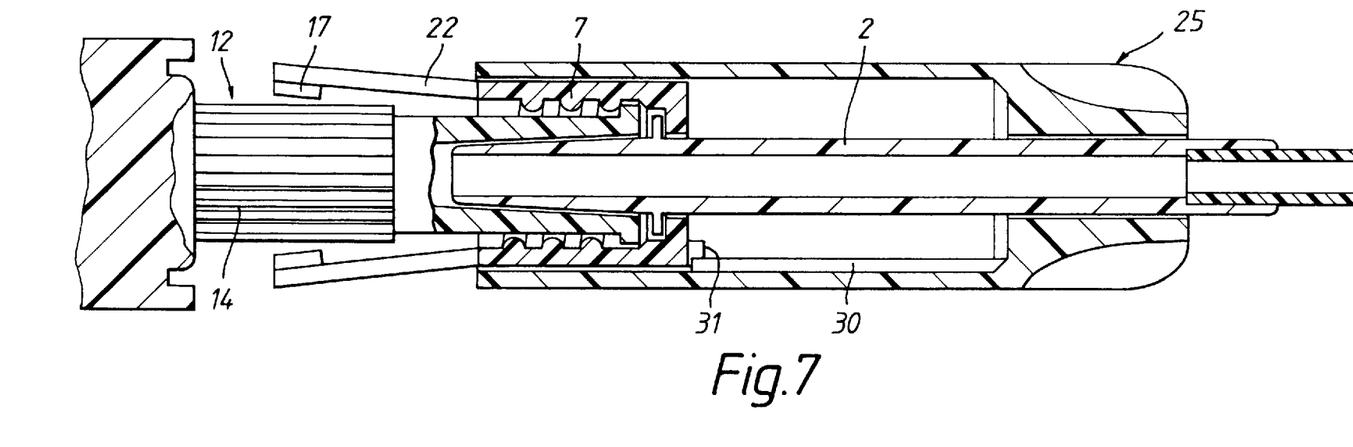
FIG. 7 is a view similar to FIG. 4 illustrating a modified construction.
Figure 8:
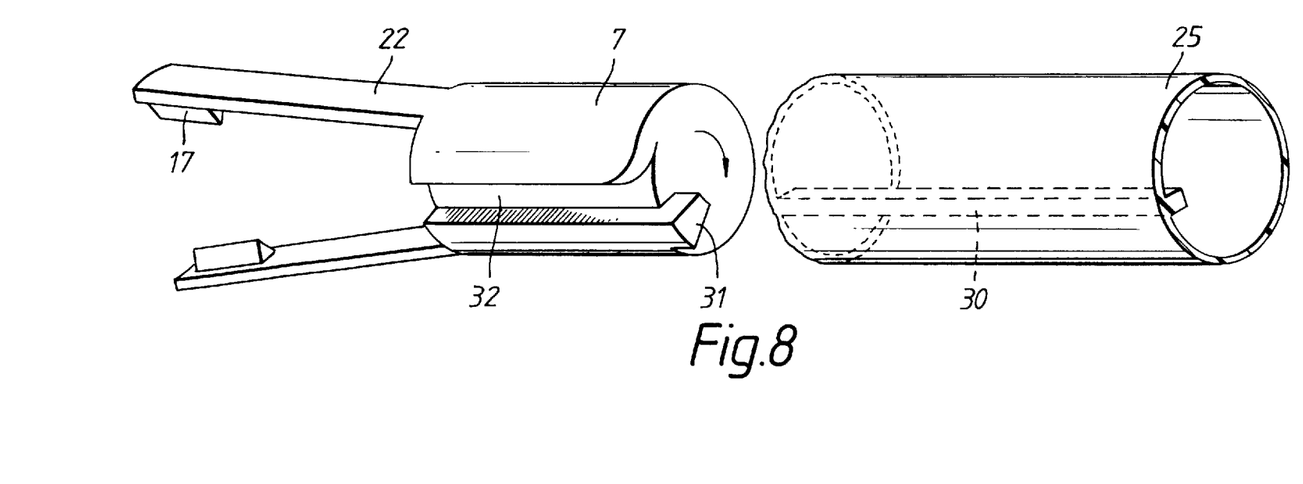
FIG. 8 is a perspective sketch showing the principles of the modified construction.

Other arrangements for interengaging the shell and cap are possible while retaining essentially the same principles of operation. Thus, in FIGS. 7 and 8 there is shown a construction in which a longitudinal rib 30 is formed on the inside of the shell and the cap has a dog 31 on its rear wall as well as a longitudinal groove 32. The rib 30 engages the dog 31 for rotating the cap to screw it onto the female member, after which the shell 25 is turned back to align the rib 30 with the groove 32 to allow the shell to be advanced to its closed position.

The forward end of the female member 1 has not been illustrated in FIGS. 1 to 8, but it is preferably provided with a valve device as described below.

Figure 9:
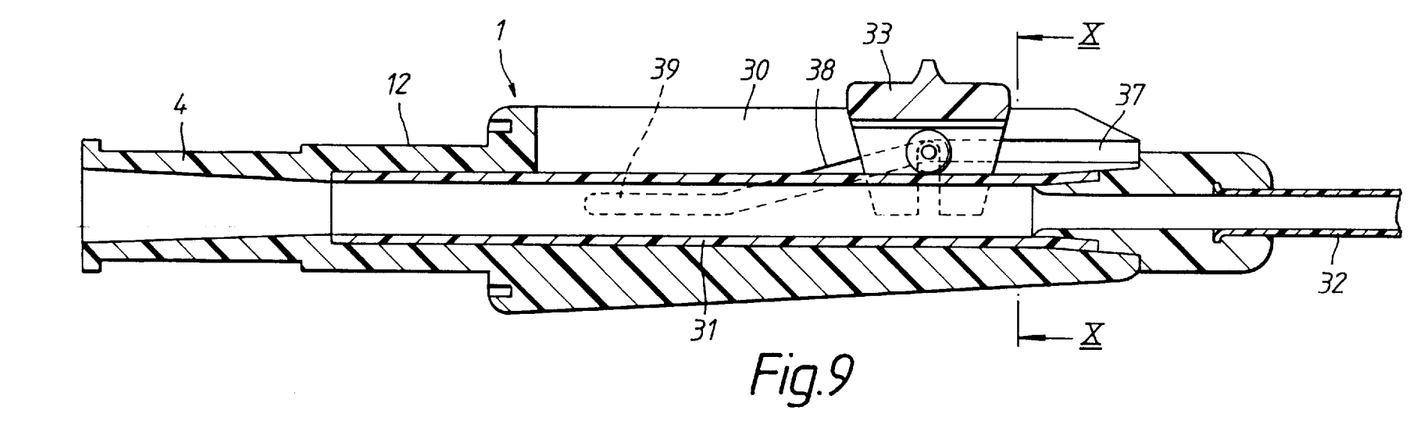
FIG. 9 shows an embodiment of a valve mechanism for the female member of a coupling.

The female member 1 shown in FIG. 9 extends forwardly to define a channel section 30 of Generally rectangular configuration. In the channel is accommodated a flexible wailed tube 31, the forward end of which is sealed to the catheter tube 22, and the rear end of which is sealed in a counterbore leading into the socket of part 4. Mounted on the channel section 30 is a slider 33 the down-turned sides of which have inturned lips which are received in longitudinal grooves provided in the external surfaces of the channel side walls. A pair of laterally spaced lugs 34 on the slider project downwardly into the channel on either side of the tube 31, and are provided with slots through which an axle pin 35 carrying a roller 36 passes. The ends of the pin engage in parallel grooves formed on the inside surfaces of the channel side walls and having upper forward sections 37, medial ramp section 38, and lower rear sections 39. In a forward position of the slider, the roller 36 is supported above the tube 31 which permits unrestricted flow through the tube. When the slider is displaced rearwardly, the pin 35 is driven down into the channel by the ramp sections 38 and causes the roller 36 to pinch the tube closed. At this time the male member will be released from the female member there being no danger of air passing through the catheter or fluid escaping. Further displacement of the slider will cause the pin to move along the lower sections 39 of the grooves, and the roller to move along the tube 31 to displace rearwardly the liquid therein behind the sealing point so that the vacated socket becomes completely filled with the liquid and hence there is no danger of air being trapped in the socket when another male member is connected to the female member. When such connection has been made the slider is moved back to its forward position to re-open the tube and allow liquid to flow once more.

Figure 12:
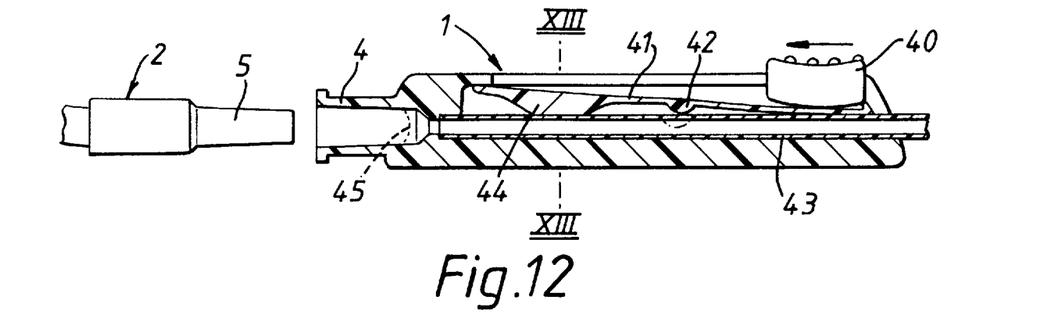
FIG. 12 is a schematic side view of another valve device.
Figure 13:
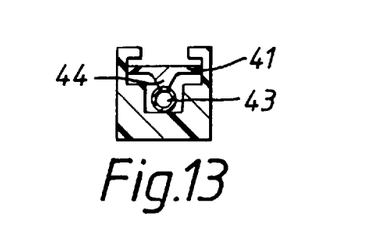
FIG. 13 is a section taken along the line XIII—XIII of FIG. 12.
Figure 14:
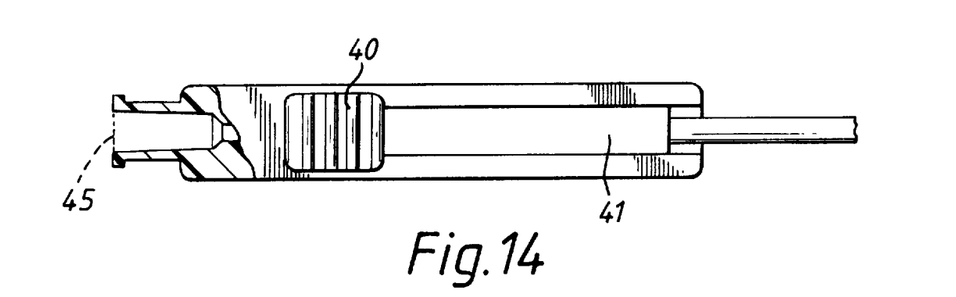
FIG. 14 is a plan view of the device of FIG. 12.

Other forms of valve which will first seal to interrupt flow and then force liquid back so that the liquid meniscus in the socket is displaced to the socket mouth are possible. In the alternative of FIGS. 12–14, a slider 40 is arranged to act on an elongate member 41 and during rearward displacement it firstly presses a projection 42 down to seal the underlying tube 43, after which it presses down another projection 44 on the member 41 to compress the tube behind the initial sealing position and hence displace the liquid meniscus 45 from the position shown in FIG. 12 to that shown in FIG. 14.

Figure 15:
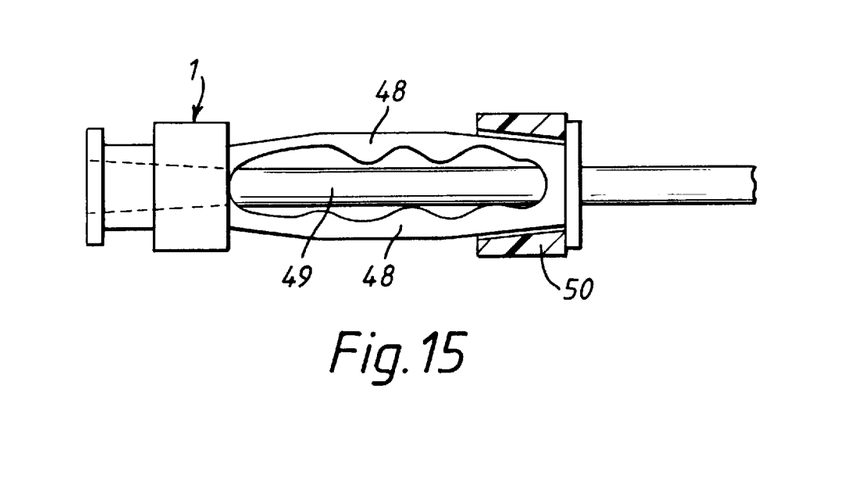
FIG. 15 shows another form of valve device.

FIG. 15 illustrates an embodiment in which a pair of opposed resilient arms 48 are positioned on opposite sides of the flexible tube 49 The outer surfaces of these arms define cam faces for cooperation with the slider 50 and the inner surfaces of the arms are shaped to pinch the tube closed and then displace the liquid towards the socket, as described above, when the slider is moved rearwardly from the forward position.

Figure 16:
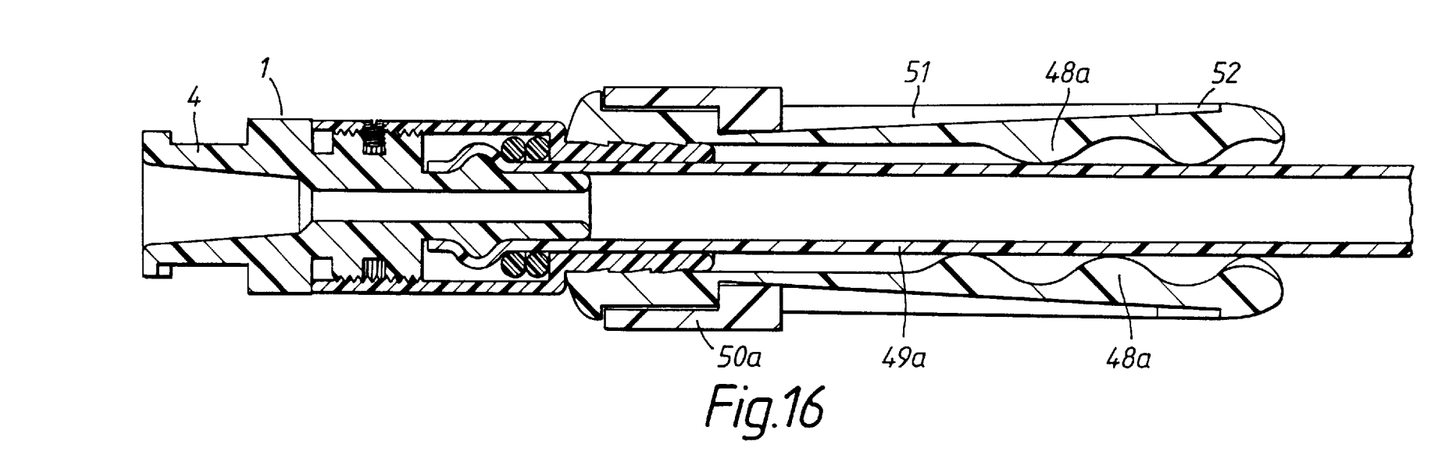
FIG. 16 is a longitudinal section through a further female member with a valve device.
Figure 17:
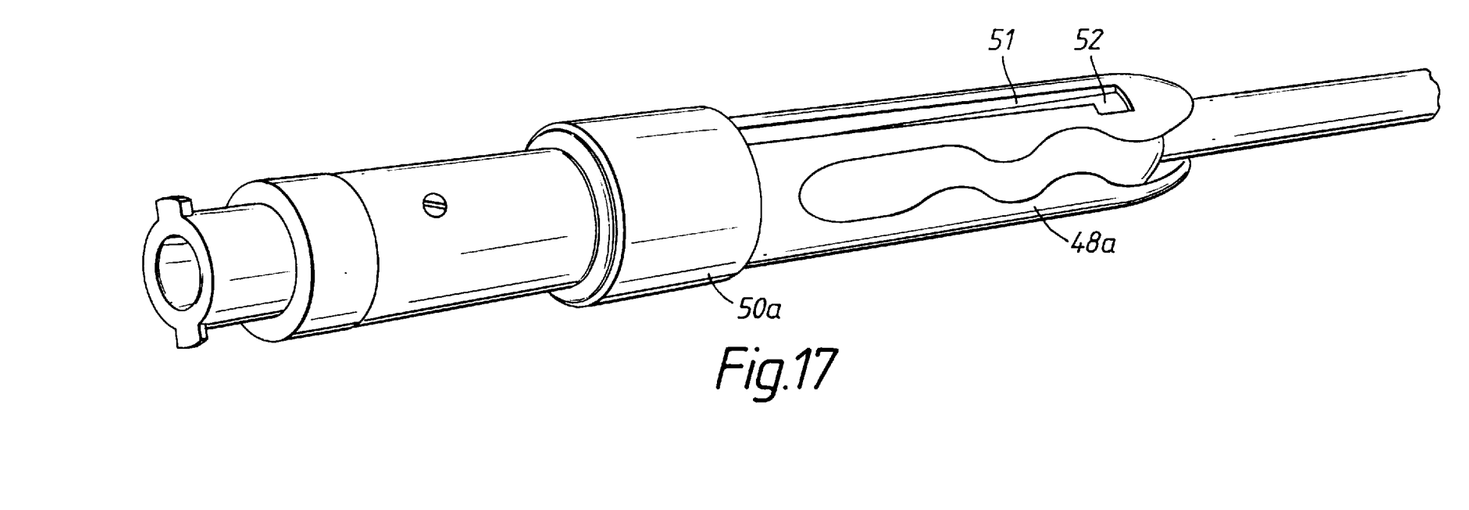
FIG. 17 is a perspective view of the member of FIG. 16.

The embodiment of FIGS. 16 and 17 is generally similar to that of FIG. 15, but in this case the resilient arms 48a have free forward ends and the slider is a collar 50a which by sliding forwardly first seals the tube 49a and then causes liquid to be displaced rearwardly behind the sealing point. The slider is guided by longitudinal grooves 51 with inclined bottom surfaces, and lateral notches 52 may be provided at the end of the grooves to enable the collar to be locked in the end position by rotating it.

It is not essential to have a slider or other device for operating the valve and the spring arms 48, 48a could instead be arranged to be pinched together such as between the thumb and forefinger.

Figures 18, 19, 20:
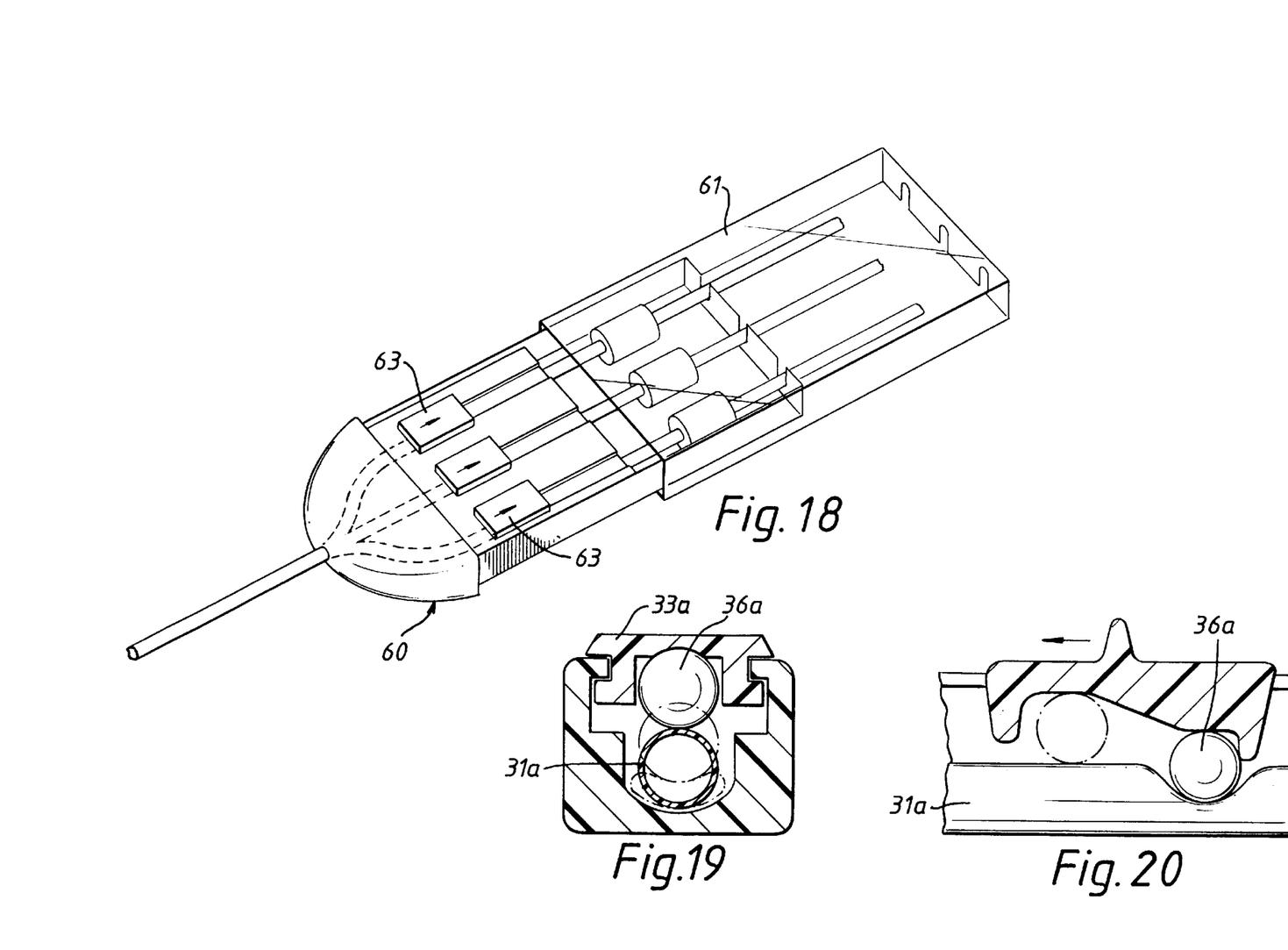
FIG. 18 is a schematic perspective view of an assembly of couplings and associated valves within a common case.
FIG. 19 is a transverse section through another valve device.
FIG. 20 is a sketch illustrating the mode of operation of the FIG. 19 device.

A group of three couplings arranged in parallel for delivery of liquid from three separate sources to a common catheter tube is shown in FIG. 18. The couplings and their associated valves are housed in a casing 60 provided with a sliding cover 61. The valves may be operated by their respective sliders 63 to control the supply of respective liquids to the catheter as well as during disconnection of the male coupling members, e.g. during connection of fresh liquid supplies.

Figure 10:
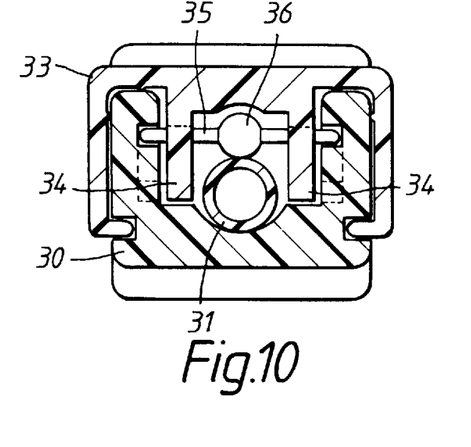
FIG. 10 is a transverse section taken along the line X—X of FIG. 9.
Figure 11:
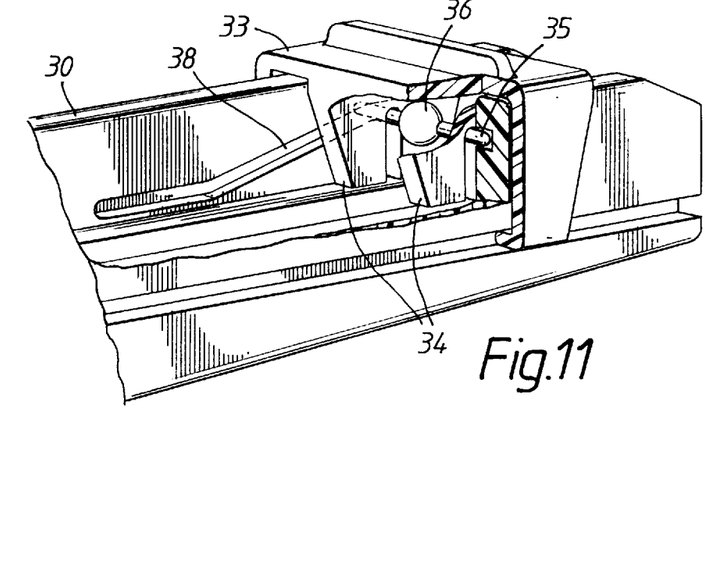
FIG. 11 is a partially cut away scrap view of the member shown in FIG. 9.

FIGS. 19 and 20 show a valve system similar in fundamental respects to that of FIGS. 9–11. A ball 36a is trapped between the slider 33a and the flexible tube 31a, and the slider has a ramp surface so that when the slider is displaced rearwardly the ball rolls along the ramp surface and presses down on the tube to pinch it closed. As the slider continues to move, the ball is carried along with it and displaced the liquid in the tube behind the initial sealing position to move back the meniscus.

Figure 21:
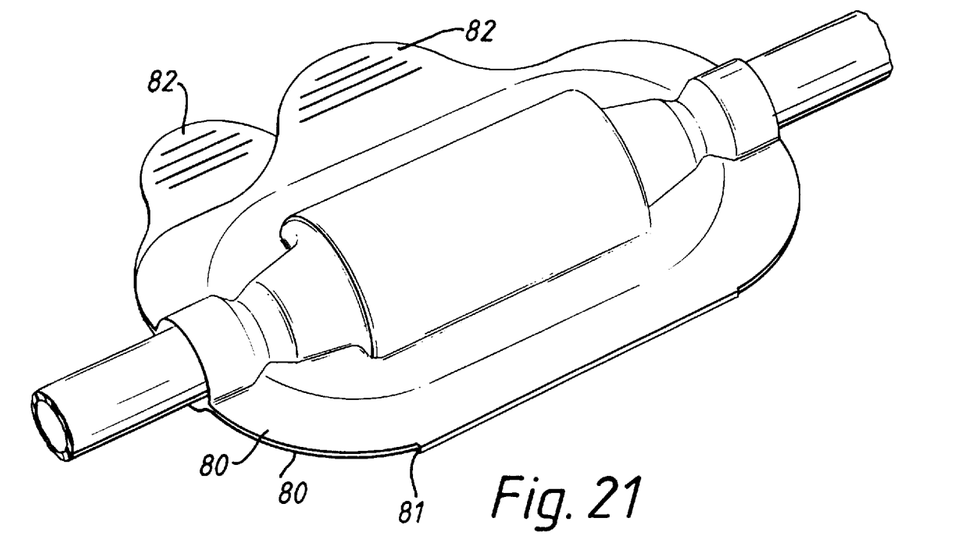
FIG. 21 is a perspective view of a capsule enclosing a coupling according to the invention.

To further assist in maintaining sterility and/or preventing unintentional disconnection, the fluid coupling of the invention and as described above is provided with a capsule within which it is cocooned. The capsule shown in FIG. 21 is made in two halves 80 connected by an integral hinge 81, e.g. by vacuum forming. The capsule halves have peripheral surfaces which are fixed together and sealed by impact adhesive. Relatively displaced tongues 82 are provided for breaking the capsule open when access to the enclosed coupling is required.

Figure 22:
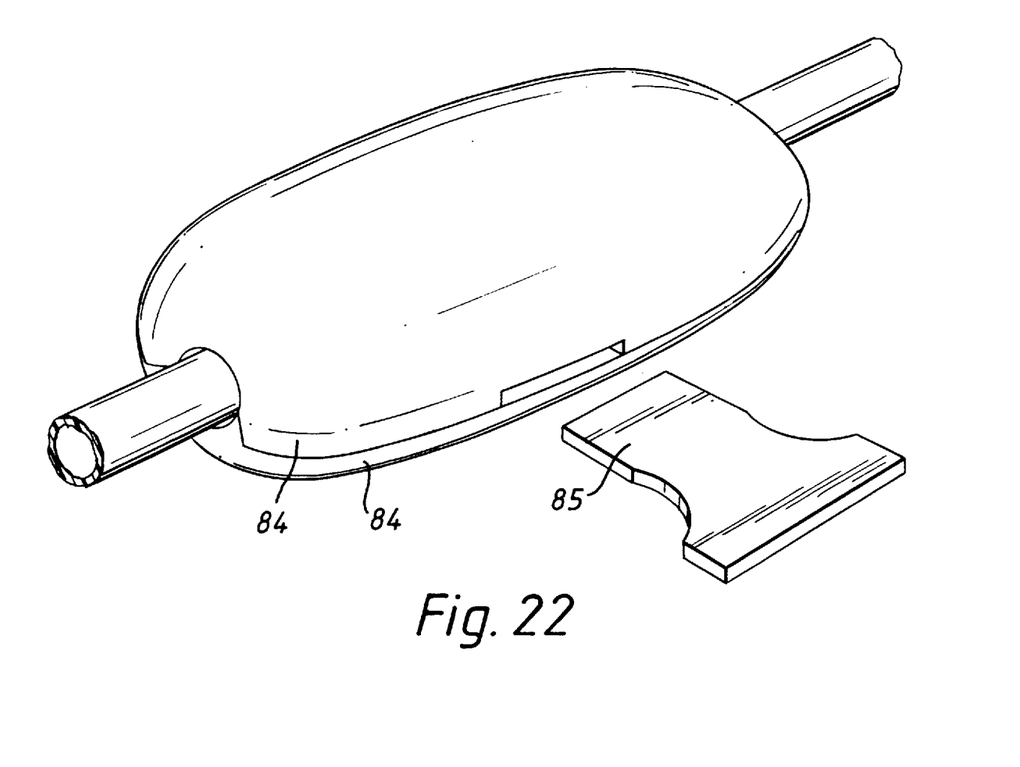
FIG. 22 is a perspective view of another capsule.

The capsule of FIG. 22 is of rigid construction and has two parts 84, either separate or hinged, which are fixed together with a snap connection. For breaking the capsule open a key 85 is inserted into the slot 86 and twisted. The interior of the capsule is shaped around the key slot and at tube openings to define serpentine paths or labyrinth type seals to deter entry of bacterial and other contaminants. Such a seal arrangement is illustrated in FIG. 23, the capsule or a member inserted therein being provided with elements to define a series of spaced discs 85 around a tube to form the serpentine pathway.

Figures 23, 24:
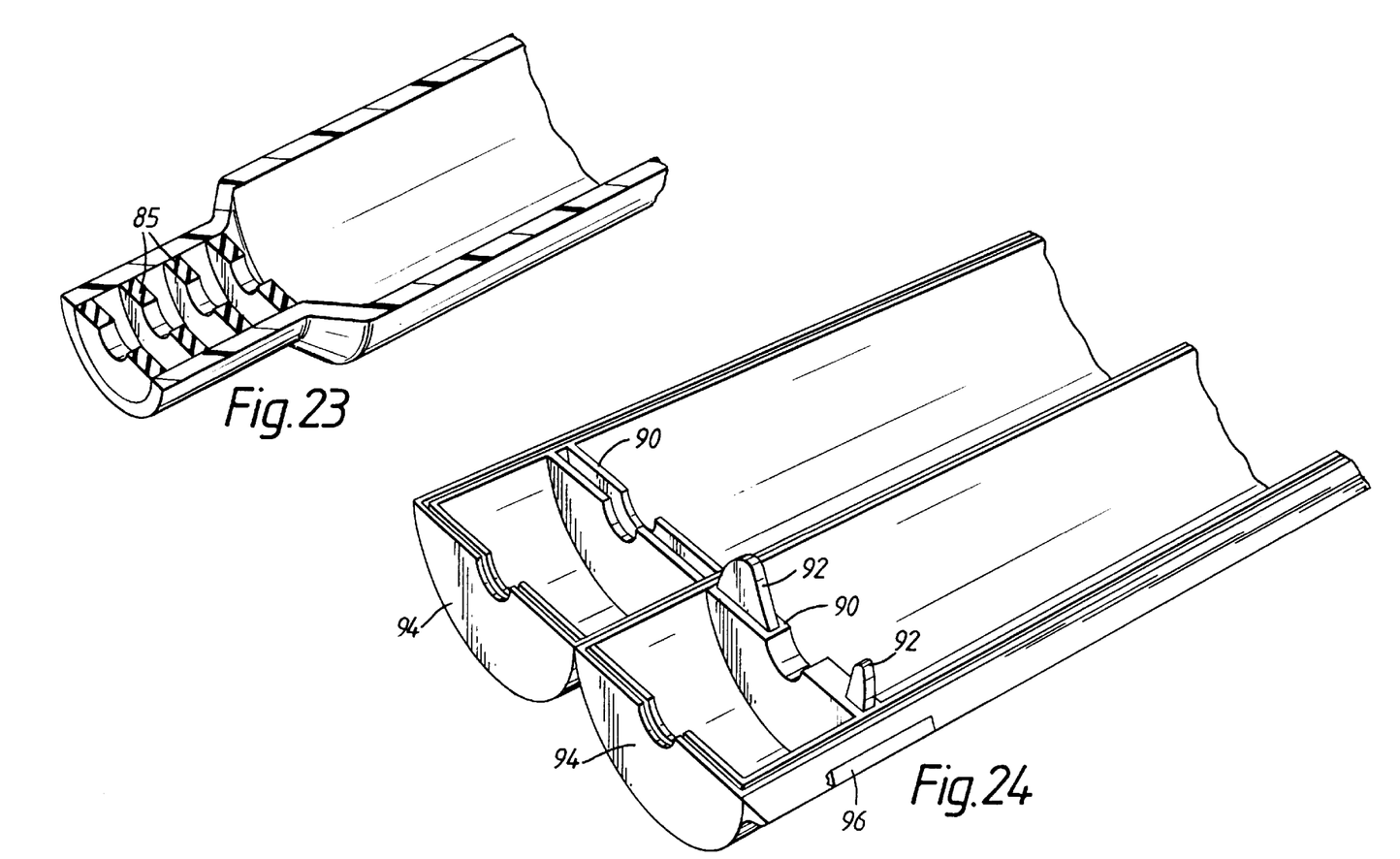
FIG. 23 illustrates a form of seal which may be incorporated in the capsules.
FIG. 24 is a partial perspective illustration of another capsule.

FIG. 24 illustrates a modification wherein the capsule halves have partition walls 90 which combine to form a disc around a tube entry opening, one partition wall being slotted and the other having location lugs 92 for ensuring correct alignment of these walls. The partition walls 90 confine with end wall elements 94 a space which may accommodate a sealing material, or sealing inserts such as a member shaped to form spaced discs as in FIG. 23. One half of the capsule has a snap latch 96 along its free longitudinal edge for engaging the corresponding edges of the other capsule half to secure the two halves in the closed condition.

Figure 25:
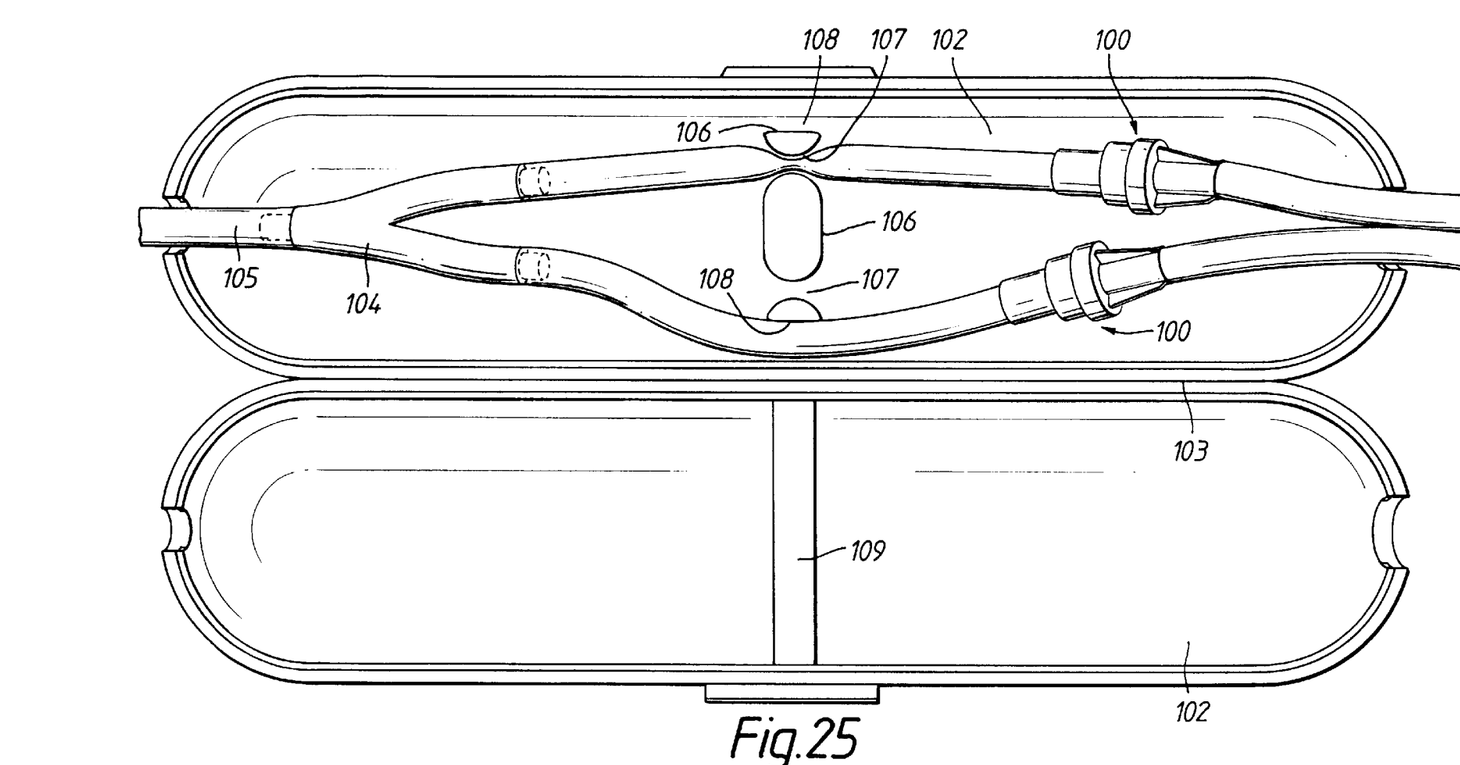
FIG. 25 shows in open condition another capsule according to the invention.

In FIG. 25 there is illustrated a capsule for use with a coupling which does not have a valve device enabling fluid flow to be closed off. The capsule is adapted to accommodate two couplings 100. As in the previous embodiments it has two parts 102 connected by a hinge 103. By means of a Y connector 104, the two couplings lead to a common tube 105 for delivering liquid thereto supplied from respective sources. Formed within one capsule part is a barrier 106 which defines two narrow slots 107 and two larger openings 108. When a tube is pressed into a narrow slot it is pinched closed to interrupt flow of liquid from the associated supply, but when it is located in a large opening 108 it allows free flow of liquid therethrough. Thus, merely by appropriate positioning of the tubes it can be determined that either, both or neither fluid supplies will be in fluid communication with the tube 105. The second capsule half has a transverse rail 109 for holding the tubes in their enquired positions in the slots 107, 108. In this embodiment it is preferred that the capsule be capable of being repeatedly opened and closed. Although not shown, the capsule is preferably provided with means for sealing around the tubes passing into and out of the capsule, e.g. as described above.

Figure 26:
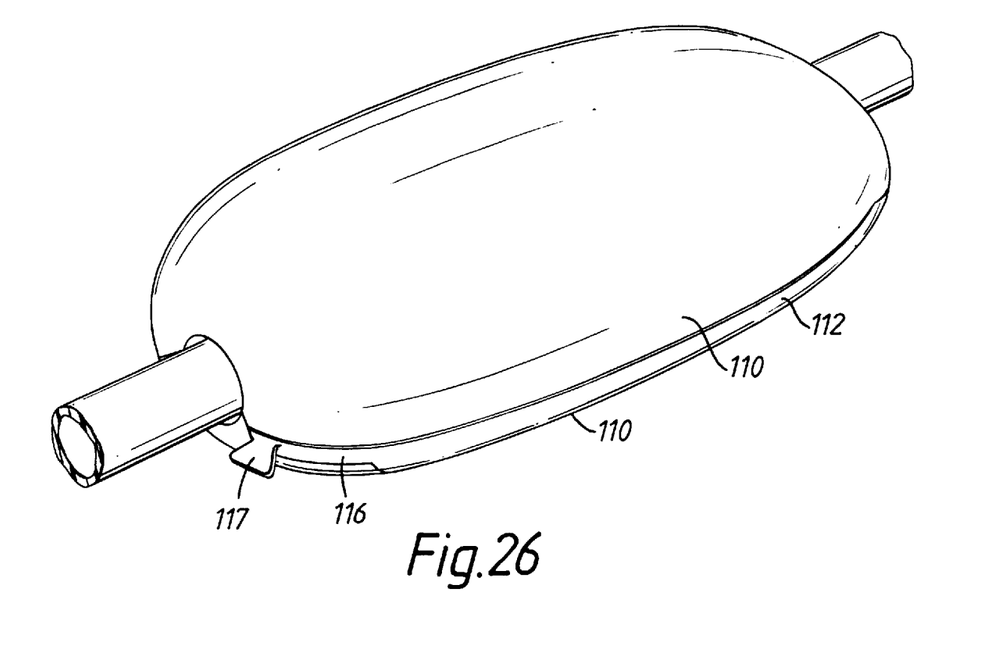
FIG. 26 shows in perspective another embodiment of a capsule.
Figure 27:
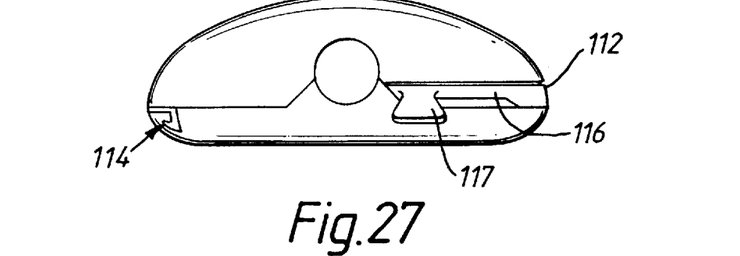
FIG. 27 shows the capsule of FIG. 26 in end elevation.

The capsule shown in FIGS. 26 and 27 is adapted for one time use, the two halves 110 being attached by an integral hinge 112 and having a snap lock mechanism 114 to fasten them securely in the closed condition.

So that the capsule may be opened to gain access to the coupling cocooned within it, a tear strip 116 with a tab 117 is provided. When this strip is torn away, the hinge is destroyed allowing the two halves to be separated. Once the tear strip 116 has been removed, the capsule is incapable of being reclosed and resealed without its intended method of use being abused.

We claim:

1. A coupling for a medical catheter comprising separate male and female members (1,2) which are connectable with a push fit, and a cap (7) coupled to the male member for surrounding the members and rotatable for releasable engagement with the female member for securing the members against being pulled apart, locking means on the cap and female member engageable to lock the cap against rotation in the loosening direction, wherein the cap (7) is rotatable by manually gripping and turning a holding section axially remote from the engagement between the male and female members, the holding section allowing the cap to be held during connection of the male and female members and during rotation of the cap relative to the female member, and wherein the locking means (14,17) are brought into engagement by axial displacement of an axially adjustable member (25) after the cap (7) has been rotated into securing cooperation with the female member.

2. A coupling according to claim 1, wherein the female member is provided with a valve including a flexible-walled tube (31), an element (36;36*a*) actuable by a slide member (33,33*a*) to pinch closed the tube upon axial sliding movement of the slide member to a valve closed position.

3. A coupling according to claim 1, wherein a separate capsule (13,25) is provided to form a substantially sealed enclosure around the connection between the male and female members.

4. A coupling according to claim 1, wherein the axially adjustable member is a shell member (25) for defining an enclosure around the cap and around the connection between the male and female members, the holding section is provided on the shell member the shell member is adjustable axially relative to the cap from a retracted position, wherein the cap is rotatable by the shell member, to an advanced position wherein the locking means (14,17) is engaged and the enclosure is formed by the shell member.

5. A coupling according to claim 4, wherein the locking means comprise at least one pawl (17) carried by the cap and locking protrusion means (14) disposed around the periphery said one member.

6. A coupling according to claim 5, wherein the or each pawl (17) is coupled to the cap by resilient means (16;22) to enable unlocking.

7. A coupling according to claim 6, wherein the or each pawl (17) is carried by a resilient ring (16) of elliptical form.

8. A coupling according to claim 6, wherein the or each pawl is carried on a resilient arm (22).

9. A coupling according to claim 8, wherein the protrusion means comprise ratchet teeth (14) disposed around said one member.

10. A coupling for a medical catheter comprising separate male and female members (1,2) which are connectable with a push fit, and a cap (7) for surrounding the members and rotatable for releasable adjustment with one of the members for securing the members against being pulled apart, and a shell member (25) for defining an enclosure around the cap and around the connection between the male and female members, wherein the shell member is adjustable axially relative to the cap from a retracted position, wherein the cap is rotatable by the shell member to an advanced position in which the shell member is rotatable relative to the cap, the shell member defining a holding section allowing the cap to be manually rotated into engagement with said one of the male and female members by holding the shell member remote from the cap.

11. A coupling according to claim 10, wherein said holding means (20) extends rearwardly of the cap.

12. A coupling according to claim 10, wherein the shell member and cap have means (27,28,29;30,31,32) cooperating to enable the cap to be rotated by means of the shell member in an axially retracted position of the shell member and to guide the shell member for axial adjustment relative to the cap between the retracted and advanced positions.

13. A coupling according to claim 12, wherein the shell member (25) is arranged to displace the pawl into engagement with the locking protrusion means (14) during axially forward adjustment of the shell member.

14. A coupling member according to claim 2, wherein the element (36;36*a*) actuated by the slide member is arranged to pinch the tube (31;31*a*) closed at an initial sealing location and to progressively collapse the tube rearwardly from the initial sealing location.

15. A coupling member according to claim 14, wherein the element comprises a rolling element (36;36a).

16. A coupling member according to claim 15, wherein an element is arranged to pinch closed the tube at an initial sealing location and then to compress the tube rearwardly of the initial sealing location.

17. A coupling according to claim 16, wherein the tube is pinched and compressed by opposed parts (48;48a;41) which are moved together to pinch and compress the tube.

18. A coupling according to claim 1, wherein the enclosure means comprises a capsule for encasing the connected members.

19. A coupling according to claim 1, wherein the capsule comprises two parts which are secured together by fastening means arranged to be destroyed by opening the capsule.

20. A coupling according to claim 19, wherein the capsule parts are hinged together.

21. A coupling according to claim 19, wherein the capsule has openings for tubes connected to the respective coupling members, and sealing means (85) are provided at said openings for cooperation with said tubes.

22. A coupling according to claim 21, wherein one of the coupling members is connected to a flexible tube, and barrier means (106) is provided within the capsule and defines a slot into which the tube is selectively positionable for pinching closed said tube.

\* \* \* \* \*